United States Patent [19]

Fahmy

[11] Patent Number: 4,683,224

[45] Date of Patent: Jul. 28, 1987

[54] N-FORMYL PHOSPHONAMIDOTHIOATES AS PESTICIDES

[75] Inventor: Mohamed A. H. Fahmy, Modesto, Calif.

[73] Assignee: E. I. Du Pont de Nemours and Company, Wilmington, Del.

[21] Appl. No.: 885,161

[22] Filed: Jul. 21, 1986

Related U.S. Application Data

[63] Continuation-in-part of Ser. No. 777,379, Sep. 18, 1985, abandoned.

[51] Int. Cl.⁴ .......................... A01N 57/02; C07F 9/44
[52] U.S. Cl. ..................................... 514/120; 558/178
[58] Field of Search ................. 558/178; 514/137, 120

[56] References Cited

U.S. PATENT DOCUMENTS 3,716,600  2/1973  Magee ................................ 558/178

OTHER PUBLICATIONS

Ciba–Geigy, "Chem. Abstracts", vol. 104: 109957j.

Primary Examiner—Anton H. Sutto

[57] ABSTRACT

Compounds of the formula

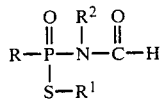

wherein the symbols have assigned meanings, and their use as insecticides, miticides and/or nematicides.

10 Claims, No Drawings

N-FORMYL PHOSPHONAMIDOTHIOATES AS PESTICIDES

This application is a continuation-in-part of application Ser. No. 777,379, filed Sept. 18, 1985, now abandoned.

DESCRIPTION OF THE INVENTION

It has been found that insecticidal, acaricidal and nematicidal activity is possessed by compounds of the formula

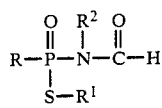

(I)

wherein R is alkyl or alkenyl of up to six carbon atoms, phenyl or benzyl, $R^1$ is straight-chain alkyl of three to five carbon atoms, branched-chain alkyl of three to six carbon atoms, phenyl or benzyl, and $R^2$ is hydrogen, alkyl, alkenyl or alkynyl of up to six carbon atoms, or alkyl of one to six carbon atoms substituted by phenyl; phenyl or phenyl substituted by one to three substituents selected from alkyl of one to six carbon atoms and halogen. It has been found that some of the compounds control insects and nematodes in soil, as well as insects and mites attacking the above-ground portions of plants. Furthermore, it has been found that compounds of the invention act systemically—that is, when applied to the plant, a compound of the invention penetrates into the cells and vascular system of the plant and is translocated therein and thereby disseminated throughout the plant without injury to the plant, yet effectively kills insects and mites that chew upon tissues of the plant or suck juices from the plant.

In these compounds, each alkyl moiety represented by R and $R^2$ may be straight-chain or branched-chain. Preferred alkenyl moieties are ethenyl, 3-methyl-2-propenyl and 2-propenyl (especially preferred). Preferred phenyl-substituted alkyl moieties are benzyl and 2-phenethyl, (benzyl being especially preferred). Preferred phenyl moieties ($R^2$) are phenyl substituted by one to three substituents selected from chlorine and alkyl moieties of one to three carbon atoms.

A preferred subclass of the compounds of Formula I is composed of those species wherein R is alkyl, $R^1$ is alkyl and $R^2$ is alkyl, as these are defined in Formula I.

The compounds of Formula I can be prepared by treating a phosphonamidothioate of the formula:

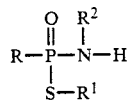

(II)

with an anhydride of formic acid and an alkanoic acid of from two to eight carbon atoms. The preferred anhydride is acetic formic anhydride, which is conveniently prepared by mixing formic acid with acetic anhydride, at a temperature of from about 0° C. to about 20° C., then heating the mixture to and at about 40°–50° C. for 15–20 minutes, then cooling it, in analogy to the method of V. C. Mehlenbacher, Organic Analysis, Interscience Publishers (1953), at page 37. At least one equivalent of acetic anhydride is used per equivalent of formic acid, and preferably an excess of the acetic anhydride is used, a 5–25% excess being suitable. In two particular instances, acetic formic anhydride was prepared as follows:

(a) Under nitrogen, 4.7 g of 96% formic acid (0.094 mole of formic acid) was added drop-by-drop to 10.0 g (0.098 mole) of stirred acetic anhydride at 0° C. After 30 minutes at 0° C., the mixture was warmed to 50° C., held there for 15 minutes, then cooled for use as a reagent.

(b) Under nitrogen, 335 g (7.28 moles) of formic acid was added to 891 g (8.73 moles) of stirred acetic anhydride at room temperature. The temperature of the mixture slowly rose to 41° C., then the mixture was stirred at 40° C. for one hour, and cooled for use as a reagent.

Alternatively, the anhydride can be prepared from acetyl chloride and sodium formate according to the procedure described in "Reagents for Organic Synthesis", M. Fieser and L. Fieser, volume 2, page 10, Wiley-Interscience (1969). Further, the anhydride can be prepared in situ in the reaction mixture, as by first adding the acetic anhydride to the phosphonamidothioate, and then adding the formic acid, or vice versa, the former procedure being preferred.

The treatment of the phosphonamidothioate with the anhydride is effected by mixing the two reagents. In many cases, no solvent will be required or desirable; in other cases it may be found that a solvent is required, or is desirable. Suitable as the solvent is a chlorinated alkane, such as methylene dichloride or 1,2-dichloroethane. In some cases, it may be desirable to mix the reagents at a low temperature (about 0° C. is suitable) and then warm the mixture to room temperature or somewhat above—for example up to about 50° C.—and hold it at that temperature until the reaction is complete. In some cases, the reagents can be mixed at room temperature. Generally, it will be desirable to employ a moderate stoichiometric excess—up to about 50–100%—of the anhydride relative to the phosphonamidothioate. Water should be excluded from the reaction mixture—as by using anhydrous reagents and conducting the treatment under nitrogen—i.e., in a nitrogen atmosphere. The product is isolated and purified by conventional techniques, as demonstrated in Examples 1–3.

The phosphonamidothioate precursors can be prepared by treating the appropriate phosphonothioic chloride of the formula

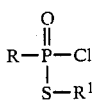

(III)

with the appropriate primary amine

(IV)

—i.e., ammonia ($R^2$=H) or other amine ($R^2$=alkyl, phenyl, benzyl), in analogy to the procedure described by J. I. G. Cadogan, Journal of the Chemical Society (London), 1961, pages 3067–3070. The treatment may be conducted by adding a solution of the amine in a suitable inert solvent, such as ether or acetone, to a solution of the chloride in a suitable inert solvent, such as acetone, at a low temperature (e.g., 5°–10° C.) then allowing the mixture to warm to room temperature—or warming it if necessary—and holding it at that temperature until the reaction is complete. It has been found that a higher yield of the desired product generally is obtained if water is excluded from the reaction system. Isolation of the product is effected by conventional techniques, as shown in Examples 1-3.

The phosphonothioic chloride precursor can be prepared by a method analogous to that described in U.S. Pat. No. 4,391,760 for preparing the corresponding phosphonothioic chloride—i.e., by treating a phosphonic dichloride of the formula

  (V)

with the appropriate thiol, $R^1$—SH, in the presence of an inert solvent and an amine base as hydrogen chloride acceptor. Aromatic hydrocarbons, such as toluene, are suitable as the solvent. Any tertiary amine base is suitable, but the trialkylamines appear to be most suitable. Water should be excluded from the reaction mixture—as by using anhydrous reagents and conducting the treatment under nitrogen. Isolation of the product is effected by conventional techniques, vide Examples 1-3.

The phosphonothioic chloride of Formula III also can be prepared by the method described by A. A. Neimysheva, et al., Journal of General Chemistry, U.S.S.R. (English), 1966, volume 36, pages 520-525—i.e., by slowly adding the appropriate sulfenyl chloride $R^1$—S—Cl  (VI)

to a stirred solution of the appropriate phosphonous dichloride of the formula

  (VII)

in sulfur dioxide at a low temperature—e.g., $-15°$ C. to $-70°$ C.—then warming the resulting mixture to room temperature, stripping it of volatiles and vacuum distilling the residue to give the product.

Those phosphonothioic chlorides wherein $R^1$ is alkyl also can be prepared by the method which is the subject of application Ser. No. 777,116—that is, treating a S,S-di-$R^1$ R-phosphonodithioate of the formula

  (VIII)

wherein both of $R^1$ are the same, with a chlorinating agent selected from sulfuryl chloride and chlorine.

Suitably, the treatment is conducted by adding the chlorinating agent to a stirred solution of the dithioate in an inert solvent, at a temperature of about 0°-10° C. Suitable solvents are the haloalkanes, such as methylene dichloride and carbon tetrachloride. Water should be excluded from the reaction mixture—as by using anhydrous reagents and conducting the treatment under nitrogen—i.e., in a nitrogen atmosphere. Preferably a slight stoichiometric excess—up to about 10% excess—of the chlorinating agent is used, relative to the dithioate. Isolation and purification of the product is accomplished by conventional techniques. In many cases, the by-product $R^1$-sulfenyl chloride is a low-boiling material that is easily removed by evaporation techniques.

The dithioate precursors (formula VIII) can be prepared by known methods. Conveniently, they can be prepared by treating the appropriate alkylphosphonic dichloride (V) with two equivalents of the appropriate thiol, $R^1$—SH, which may be in the form of its alkali metal salt, in the presence of an inert solvent and two equivalents of a hydrogen chloride acceptor.

Compounds of Formula I also can be prepared by forming a metal salt (for example the lithium salt) of a phosphonamidothioate of Formula II, and treating the salt with the appropriate formic/alkanoic acid anhydride. Example 46, hereinafter, illustrates the procedures: a suitable organo derivative of the metal, such as n-butyllithium, is slowly added to a solution of the precursor of Formula II in a suitable solvent, such as tetrahydrofuran (THF), at a low temperature, for example $-50°$ C. to $-70°$ C., moisture and oxygen being excluded, then the anhydride is slowly added and the mixture is warmed, to complete the reaction.

The preparation and isolation of particular individual species of the genus of Formula I, is described in the Examples, hereinafter. Other typical individual species are the following each identified in terms of the symbols of Formula I:

| Species | R | $R^1$ | $R^2$ |
| --- | --- | --- | --- |
| A | propyl | 1,1-dimethylpropyl | hydrogen |
| B | 1-methylethyl | 1,1-dimethylpropyl | 2-methylpropyl |
| C | methyl | 1,1-dimethylpropyl | 2-methylpropyl |
| D | methyl | 1,1-dimethylpropyl | methyl |
| E | ethyl | 1-methylbutyl | hydrogen |
| F | ethyl | 1-methylbutyl | 2-propynyl |
| G | ethyl | 1-methylbutyl | phenyl |
| H | 1-methylethyl | 1,1-dimethylpropyl | 2-methylpropyl |
| I | propyl | 1,1-dimethylpropyl | ethyl |
| J | ethyl | 1,1-dimethylpropyl | 3,3-dimethylpropyl |
| K | ethyl | 1-methylbutyl | methyl |
| L | ethyl | 1-methylbutyl | hydrogen |
| M | 1-methylethyl | 1-methylbutyl | hydrogen |
| N | 1-methylethyl | propyl | ethyl |
| O | ethyl | 1-methylbutyl | 2-methylpropyl |
| P | ethyl | 1,1-dimethylpropyl | hydrogen |
| Q | methyl | propyl | hydrogen |
| R | ethyl | butyl | hydrogen |
| S | ethyl | 2-methylpropyl | hydrogen |
| T | ethyl | 2-methylpropyl | 2-methylpropyl |

The preparation, isolation and testing of individual species of the genus of Formula I, in particular instances, are described in the following examples. In each case, the identity of each of the products, and each of the precursors, was confirmed as necessary by appropriate chemical and spectral analyses.

EXAMPLE 1

S-(2-methylpropyl)P-ethyl-N-formyl-N-methylphosphonoamidothioate (1)

Under nitrogen, 10.56 g of sulfuryl chloride was added drop-by-drop to 6.50 g of 2-methyl-1-propanethiol. Under nitrogen, the resulting solution was added drop-by-drop over 45 minutes to a solution of 10.41 g of ethylphosphonous dichloride in 25 ml of sulfur dioxide at $-60°$ C. After 30 minutes the mixture was allowed to warm slowly to room temperature and then stripped of solvent. The residue was distilled in a Kugelrohr apparatus to give S-(2-methylpropyl)ethylphosphonochloridothioate (1A), as a yellow liquid, b.p.: 90° C., 1.3 Torr.)

2.51 g of methylamine (as a 40% solution in water) was added drop-by-drop to a solution of 2.60 g of 1A in 5 ml of acetone at 0°–18° C. The mixture was allowed to warm to room temperature, held there for 1.5 hours, then stripped of solvent. The residue was partitioned between methylene chloride and water. The methylene chloride phase was separated, dried (Na$_2$SO$_4$) and stripped of solvent. The residue was flash chromatographed over silica gel, using a 1:1 v:v mixture of ethyl acetate and acetonitrile as eluent, giving S-(2-methylpropyl)P-ethyl-N-methylphosphonamidothioate (1B), as a yellow liquid, boiling point not determined.

1.5 ml of freshly prepared acetic formic anhydride was added to 0.20 g of 1B at 0° C., then the resulting solution was held at room temperature for 95 hours, diluted with ether and washed with saturated sodium bicarbonate solution. The organic phase was separated, dried (Na$_2$SO$_4$) and stripped of solvent. The residue was chromatographed over silica gel, using ethyl acetate as eluent, to give 1, as a yellow liquid, boiling point not determined.

EXAMPLE 2

S-(1-methylpropyl)P-ethyl-N-formyl-N-methylphosphonamidothioate (2)

Under nitrogen, 7.0 ml of triethylamine was added drop-by-drop over 4 minutes to a stirred mixture of 7.3 g of ethylphosphonic dichloride, 4.5 g of 1-methyl-1-propanethiol and 40 ml of toluene at 5°–10° C. The mixture was stirred at 5° C. for 2 hours, at room temperature for 3 days, then filtered. The filtrate was stripped of solvent to give S-(1-methylpropyl)ethylphosphonochloridothioate (2A), as an amber liquid.

2A was dissolved in 50 ml of dry acetone, and 8.0 g of a 40% aqueous solution of methylamine was added, with stirring, at room temperature. The resulting mixture was stirred at room temperature for 6 days, then stripped of solvent. The residue was vacuum chromatographed over silica gel, first using ethyl acetate, then ether, as eluents, to give S-(1-methylpropyl)P-ethyl-N-methylphosphonamidothioate (2B) as an amber liquid, boiling point not determined.

5.5 equivalents (0.012 mole) of freshly prepared acetic formic anhydride was mixed with 2.4 g of 2B. The mixture was stirred at room temperature for 1 day, then extracted with ether. The extract was washed with saturated aqueous sodium bicarbonate solution, dried (MgSO$_4$), and stripped of solvent. The residue was vacuum chromatographed over silica gel, using methylene chloride as eluent, to give 2, as an amber liquid, boiling point not determined.

EXAMPLE 3

S-(propyl)P-ethyl-N-formyl-N-methylphosphonamidothioate (3)

Under nitrogen, 10.14 g of sulfuryl chloride was added drop-by-drop to 6.3 ml of 1-propanethiol, at 0° C. The resulting solution was added drop-by-drop over 45 minutes to a solution of 10.0 g of ethylphosphonous dichloride in 25 ml of sulfur dioxide at −70° C. After 10 minutes, the mixture was allowed to warm slowly to room temperature and then stripped of volatiles. The residue was distilled under reduced pressure, to give S-propyl ethylphosphonochlorothioate (3A), as a yellow liquid, b.p.: 70° C., 0.4 Torr.

2.29 g of methylamine, as a 40% solution in water, was added to a solution of 2.29 g of 3A in 5 ml of acetone, at 5° C. The mixture was allowed to warm to room temperature and held there for 15 hours, then stripped of solvent, and the residue was partitioned between methylene chloride and water. The organic phase was separated, dried (Na$_2$SO$_4$) and stripped of solvent. The residue was flash chromatographed over silica gel, using a 1:1 v:v mixture of acetonitrile and ethyl acetate as eluent, to give S-propyl P-ethyl-N-methylphosphonamidothioate (3B), as a yellow liquid, boiling point not determined.

2.50 g of freshly prepared acetic formic anhydride was added to a solution of 0.19 g of 3B in 3 ml of methylene chloride at room temperature. The temperature was held for 21 hours, then stripped of solvent under low pressure. The residue was flash chromatographed over silica gel, using ethyl acetate as eluent, to give 3, as a pale yellow liquid, boiling point not determined.

EXAMPLES 4–45

The following additional individual species of the genus of Formula I, each identified in terms of the symbols used in Formula I, were prepared from the appropriate reagents by the procedures described in Examples 1–3.

| Example No. | Compound No. | R | R$^1$ | R$^2$ | Physical State |
|---|---|---|---|---|---|
| 4 | 4 | ethyl | 1,1-dimethylethyl | methyl | white solid, m.p.: 54–57° C. |
| 5 | 5 | ethyl | 1,1-dimethylethyl | H | tan solid, m.p.: 96.5–99° C. |
| 6 | 6 | ethyl | 1,1-dimethylpropyl | methyl | amber liquid |
| 7 | 7 | ethyl | 1-methylpropyl | ethyl | yellow liquid |
| 8 | 8 | ethyl | 2-methylpropyl | 2-methylpropyl | yellow liquid |
| 9 | 9 | ethyl | 2-methylpropyl | ethyl | yellow liquid |
| 10 | 10 | ethyl | 2-methylpropyl | propyl | yellow liquid |
| 11 | 11 | ethyl | 2-methylpropyl | 2-methylpropyl | brown oil |
| 12 | 12 | ethyl | 1,1-dimethylpropyl | ethyl | pale yellow liquid |
| 13 | 13 | ethyl | 1,1-dimethylpropyl | propyl | yellow liquid |
| 14 | 14 | ethyl | 1,1-dimethylpropyl | 2-methylpropyl | pale yellow liquid |
| 15 | 15 | ethyl | propyl | 2-methylpropyl | yellow liquid |
| 16 | 16 | ethyl | 1,1-dimethylethyl | ethyl | yellow liquid |
| 17 | 17 | ethyl | 1,1-dimethylethyl | propyl | pale yellow liquid |
| 18 | 18 | ethyl | 1,1-dimethylethyl | 2-methylpropyl | pale yellow liquid |
| 19 | 19 | ethyl | propyl | ethyl | pale yellow liquid |
| 20 | 20 | ethyl | propyl | propyl | pale yellow liquid |
| 21 | 21 | methyl | 1-methylpropyl | 2-methylpropyl | pale yellow liquid |
| 22 | 22 | methyl | 1-methylpropyl | propyl | pale yellow liquid |

-continued

| Example No. | Compound No. | R | R¹ | R² | Physical State |
|---|---|---|---|---|---|
| 23 | 23 | methyl | 1-methylpropyl | ethyl | pale yellow liquid |
| 24 | 24 | ethyl | 1-methylpropyl | propyl | yellow liquid |
| 25 | 25 | methyl | propyl | methyl | pale yellow liquid |
| 26 | 26 | ethyl | butyl | ethyl | pale yellow liquid |
| 27 | 27 | methyl | propyl | propyl | pale yellow liquid |
| 28 | 28 | methyl | propyl | 2-methylpropyl | pale yellow liquid |
| 29 | 29 | ethyl | butyl | methyl | yellow liquid |
| 30 | 30 | methyl | propyl | ethyl | pale yellow liquid |
| 31 | 31 | ethyl | butyl | 2-methylpropyl | yellow liquid |
| 32 | 32 | ethyl | butyl | propyl | pale yellow liquid |
| 33 | 33 | methyl | 1-methylpropyl | methyl | yellow liquid |
| 34 | 34 | methyl | 1,1-dimethylpropyl | ethyl | pale yellow liquid |
| 35 | 35 | methyl | 1,1-dimethylpropyl | propyl | pale yellow oil |
| 36 | 36 | methyl | 1,1-dimethylpropyl | methyl | yellow oil |
| 37 | 37 | ethyl | 1-methylpropyl | hydrogen | yellow oil |
| 38 | 38 | methyl | 1,1-dimethylpropyl | 2-methylpropyl | yellow oil |
| 39 | 39 | ethyl | 1-methylpropyl | benzyl | yellow liquid |
| 40 | 40 | ethyl | propyl | benzyl | pale yellow liquid |
| 41 | 41 | propyl | propyl | methyl | yellow liquid |
| 42 | 42 | propyl | 1-methylpropyl | methyl | amber liquid |
| 43 | 43 | 1-methylethyl | propyl | methyl | pale yellow liquid |
| 44 | 44 | 1-methylethyl | 1-methylpropyl | methyl | pale yellow liquid |
| 45 | 45 | ethyl | 1-methylpropyl | 2-propynyl | yellow liquid |

EXAMPLE 46

P-methyl S-propyl N-formyl-N-(1-methylethyl)phosphonoamidothioate (46)

10.96 g of sulfuryl chloride was added slowly, drop-by-drop, to 7.0 ml of propanethiol under nitrogen at −10° C. After 20 minutes, the mixture was added drop-by-drop over 30 minutes to a solution of 10.0 g of methylphosphonous dichloride in 30 ml of sulfur dioxide under nitrogen at −70° C. After 15 minutes, the mixture was allowed to warm, slowly to room temperature, stripped of volatile material and the residue was distilled in a Kugelrohr apparatus to give S-propyl methylphosphonochlorodithioate (43A), as a colorless liquid, b.p.: 85° C./0.5 Torr.

1.23 g of 43A was dissolved in 7 ml of dry ether, under nitrogen. At 0-12° C., a solution of 1.31 g of isopropylamine in 2 ml of ether was added drop-by-drop. The mixture was allowed to warm to room temperature, then after 30 minutes was filtered. The filtrate was stripped of solvent and the residue was flash chromatographed on silica gel using ethyl acetate as eluent. One set of fractions consisted of very pale yellow liquids, identified as S-propyl P-methyl-N-(1-methylethyl)phosphonamidothioate (43B).

4.5 ml of n-butyllithium (1M in hexane) was added drop-by-drop to a solution of 1.20 g of 43B in 5 ml of dry THF, under nitrogen at −60° C. After 30 minutes, 12.5 g of acetic formic anhydride was added drop-by-drop. After 30 minutes, the mixture was allowed to warm to room temperature, and after 1.5 hours was stripped of solvent. The residue was mixed with methylene chloride and water; the layers were separated, the methylene chloride phase was dried (MgSO₄), filtered and stripped of solvent. The residue was flash chromatographed on silica gel, using a 1:1 v:v mixture of ethyl acetate and hexane as eluent, to give 43, as a pale yellow liquid.

The compounds of the invention have been found to be toxic with respect to invertebrate pests, by which is meant insects of the class Insecta and related classes of arthropods, such as the acarids (e.g., mites), ticks, spiders, wood lice and the like. In particular, they have been found to be highly toxic to mites. Further, compounds of the invention have been found to be effective for controlling insects and nematodes in soil.

For application, a compound of the invention ordinarily is applied most effectively by formulating it with a suitable inert carrrier or surface-active agent, or both. The invention, therefore, also includes compositions suitable for combatting pests, such compositions comprising an inert carrier or surface-active agent, or both, and as active ingredient at least one compound of the invention. The invention also provides a method of combatting pests at a locus, which comprises applying to that locus a compound of the invention or a pesticidal composition according to the invention.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides—i.e., horticulturally acceptable adjuvants—are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene;

petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, surcrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25–75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3–7% by weight of a blend of surfactants, which act as wetting, dispersing, suspending and binding agents, and 1–3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.0001% by weight to as much as about 95% by weight of a compound of the invention as the active ingredient.

The compositions of the invention may also contain other ingredients, for example, other compounds possessing pesticidal, especially insecticidal, acaricidal or fungicidal properties, as are appropriate to the intended purpose.

The method of applying a compound of the invention to control pests comprises applying the compound, ordinarily in a composition of one of the aforementioned types, to a locus or area to be protected from the insects, such as the foliage and/or the fruit of plants. The compound, of course, is applied in an amount sufficient to effect the desired action. This dosage is dependent upon many factors, including the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected—i.e., the dosage which the insect contacts—is of the order of 0.001 to 0.5% based on the total weight of the formulation, though under some circumstances the effective concentration will be as little as 0.0001% or as much as 2%, on the same basis.

Activity of compounds of the invention with respect to insect and acarine pests was determined by using standardized test methods to measure the toxicity of the compounds as follows:

I. Houseflies (*Musca domestica* (Linne)) were tested by placing 50 4- to 5-day-old adult houseflies into a spray cage and spraying with 0.6 ml of a solution of test compound. After spraying, the flies were observed to ascertain any knockdown effect, and then were anesthetized with $CO_2$ and transferred to a recovery cage containing a milk pad for food. The cages were held for 18–20 hours after which mortality counts were made. Both dead and moribund flies were counted. The test were conducted employing several different dosage rates for each test compound.

II. Pea aphids (*Acyrthosiphon pisum* (Harris)) were tested by placing about 100 adult aphids on broad bean plants. The plants were sprayed with dilutions of an acetone solution of the test compound in water containing an emulsifier and held in containers under laboratory conditions for 18 to 20 hours, at which time the living aphids in the containers were counted. The tests were conducted employing several different dosage rates for each test compound.

III. Adult female two-spotted spider mites (*Tetranychus urticae* (Koch)) were tested by placing 50-75 mites on the bottom side of leaves of pinto bean plants. The leaves were sprayed with dilutions of an acetone solution of the test compound in water containing an emulsifier and kept under laboratory conditions for about 20 hours, at which time mortality counts were made. The tests were conducted employing several different dosage rates for each compound.

IV. Third instar corn earworm larvae (*Heliothis zea* (Boddie)) were tested by spraying broad bean plants with dilutions of an acetone solution of the test compound in water containing an emulsifier. Immediately after spraying, 5 larvae were transferred to the plant and held for 44-46 hours, at which time the dead and moribund larvae were counted. The tests were conducted employing several different dosage rates for each test compound.

In the case of each species of insect, the concentration of the test compound by weight in the formulation required to kill fifty percent of the insects—i.e., the $LC_{50}$ dosage—was determined. The results are set out in Table I.

In each set of tests, identical tests were conducted using Parathion as a standard for comparison.

In each instance, the toxicity of the test compound was compared to that of a standard pesticide, parathion, the relative toxicity of the test compound then being expressed in terms of the relationship between the amount of the test compound and the amount of the standard pesticide required to produce the same percentage (50%) of mortality in the test insects. By assigning the standard pesticide an arbitrary rating of 100, the toxicity of the test compound was expressed in terms of the Toxicity Index, which compares the toxicity of the test compound of the invention with that of the standard pesticide. That is to say, a test compound having a Toxicity Index of 50 would be half as active, while one having a Toxicity Index of 200 would be twice as active, as the standard pesticide. The results are set forth in Table I.

TABLE I

| Compound Number | Toxicity Index | | | |
|---|---|---|---|---|
| | House-fly | Pea Aphid | Corn Earworm | Spider Mite |
| 1 | 30 | 20 | 10 | 650 |
| 2 | 30 | 20 | 40 | 1550 |
| 3 | 25 | 20 | 45 | 7300 |
| 4 | 20 | — | 35 | 55 |
| 5 | 20 | 10 | 5 | 770 |
| 6 | 40 | 25 | 10 | 950 |
| 7 | 20 | 25 | 30 | 1400 |
| 8 | 20 | 275 | — | 1200 |
| 9 | 30 | 50 | 25 | 350 |
| 10 | 30 | 55 | 15 | 1750 |
| 11 | 20 | 40 | 10 | 700 |
| 12 | 35 | 190 | 5 | 3100 |
| 13 | 30 | 120 | 5 | 3100 |
| 14 | 35 | 90 | 5 | 4900 |
| 15 | 30 | 40 | 30 | 9200 |
| 16 | 25 | 10 | 45 | 2400 |
| 17 | 15 | 15 | 10 | 2200 |
| 18 | 5 | 15 | 10 | 2500 |
| 19 | 30 | 10 | 85 | 3200 |
| 20 | 35 | 10 | 25 | 2500 |

TABLE I-continued

| Compound Number | Toxicity Index | | | |
|---|---|---|---|---|
| | House-fly | Pea Aphid | Corn Earworm | Spider Mite |
| 21 | 25 | 60 | 110 | 500 |
| 22 | 20 | 60 | 220 | 700 |
| 23 | 20 | 35 | 210 | 750 |
| 24 | 25 | 55 | 25 | 410 |
| 25 | 15 | 5 | 160 | 800 |
| 26 | 10 | 5 | 5 | 160 |
| 27 | 15 | 5 | 180 | 700 |
| 28 | 20 | 10 | 150 | 800 |
| 29 | 10 | 5 | 10 | 650 |
| 30 | 15 | 5 | 230 | 160 |
| 31 | 5 | 5 | 0 | 750 |
| 32 | 10 | 5 | 15 | 1000 |
| 33 | 25 | 5 | 75 | 110 |
| 34 | 15 | 25 | 30 | 1200 |
| 35 | 15 | 45 | 10 | 1300 |
| 36 | 20 | 15 | 10 | 850 |
| 37 | 20 | 35 | 0 | 40 |
| 38 | 15 | 35 | 5 | 550 |
| 39 | 5 | 10 | 10 | 1700 |
| 40 | 20 | 55 | 10 | 2200 |
| 41 | 15 | 10 | 15 | 100 |
| 42 | 25 | 10 | 0 | 270 |
| 43 | 25 | 25 | 0 | 40 |
| 44 | 30 | 35 | 0 | 55 |
| 45 | 30 | 35 | 15 | 5100 |
| 46 | 5 | 15 | 85 | 380 |

In one embodiment of the invention, compounds of Formula I are used to control larvae of soil-dwelling insects that attack plants growing in the soil, the method for control of such insects comprising providing in the soil in which the plants are growing, or are to be grown, an insecticidally effective dosage of a compound of Formula I. For the same reason, the invention also embodies a method for protecting a plant from attack by insects dwelling in the soil in which the plant is growing, that method comprising providing in the soil in which the plant is growing or in which it is to be grown, an insecticidally effective dosage of a compound of Formula I.

Compounds of the Formula I may be used to control a variety of soil-dwelling insects, such as species of Diabrotica, for example, *Diabrotica virgifera virgifera, D. longicornis barberi* and *D. undecimpunctata howardi*, the western, northern and southern corn rootworms, respectively; species of Agrotis, Crymodes, Amathes, Euxoa, Peridroma, Lacinipolia, Nephelodes, Actebia, Feltia, Loxagrotis (cutworms), Agriotes, Limonius, Horistonotus, Ctenicera, Conoderus (wireworms), and the like, some of the better known species being: *Agrotis ipsilon* (black cutworm), *Agriotes mancus* (wheat wireworm) and the three Diabrotica species mentioned above.

For use as soil insecticides, the compound of Formula I suitably is applied to the soil at a rate of from about 0.01 to about 10 kilograms per hectare. Good control of soil inhabiting insects or their larvae is obtained at rates of from about 0.1 to about 5 kilograms per hectare and especially from about 0.5 to about 4 kilograms per hectare. The compound of Formula I can conveniently be formulated for use as a granule or powder containing a solid diluent, impregnated with the compound. Such formulations usually contain from about 1 to about 50% by weight of the compound. More effective control results when the formulation is physically lightly mixed with the topsoil. The mixing is preceded or immediately followed by planting seeds which germinate into plants. The compound of Formula I can be applied as a drench—that is, as a solution or dispersion of the compound in a non-phytotoxic solvent or liquid diluent, suitably water. Such drenches can be prepared by diluting with water a concentrate containing the compound of Formula I, an emulsifying agent, and preferably an organic solvent, such as toluene. The compound of Formula I can be applied by band, furrow or side-dress technqiues, and may be incorporated or not.

Activity of compounds of Formula I with respect to soil-dwelling insect pests was determined as follows:

Corn Rootworm Test

The test chemical was dissolved in acetone and the solution was mixed with water containing 0.055% Atlox 1045A. The amounts of test compound and water were so chosen as to provide 500 grams of a soil mixture containing 9% by weight of water and three parts per million (ppm) by weight of the test compound. The materials were thoroughly mixed to give a homogeneous mixture.

Sixty grams of the soil mixture was added to a 4 ounce wide-mouthed jar (until it was about half full). Two sweet corn seeds, which had been surface sterilized in 0.2% sodium hypochlorite solution for fifteen minutes and rinsed with water, were pressed into the soil near the perimeter of the jar. A small cavity of about 2.5 cubic centimeters was opened in the surface of the soil and 20 *Diabrotica undecimpunctata undecimpunctata* Mannerheim (western spotted cucumber beetle) eggs were placed in the cavity. The eggs were immediately covered with fine-sieved Zonolite or vermiculite and the covering material was wetted with about 1.5 cubic centimeters of water. The jar was then capped with a lid into which two 2.5-millimeter holes had been drilled for ventilation. The jars were held under lamps at 27° C. The eggs were generally two to four days old. Two replicates were conducted. The remainder of the soil was held in a sealed container at room temperature. Eight days later, the contents of the jar were examined for the presence of live larvae, the number thereof was recorded and the corn roots were examined for feeding damage. Compounds showing control at 1 ppm or lower rate in the first week were evaluated at subsequent weeks—i.e., at 4 and 8 weeks—so long as activity justified further testing. Each of these tests was conducted in sequence, as described above, by using samples of the soil mixture from the sealed container that had been held for the appropriate length of time. Each test period was designated by the age of the soil mixture at the beginning of the test, with the results being ascertained one week later—i.e., the test period designated as zero employed freshly prepared soil mix, results read one week later, the test period designated as two weeks employed two-week-old mix, results read one week later, etc.

The results of the tests were reported as ($LC_{50}$ dosages, parts per million (ppm) based on the amount of test chemical in the soil.)

The results are set out in Table II.

TABLE II

| Compound No. | $LC_{50}$ (ppm) at Indicated Time | | |
|---|---|---|---|
| | 0 | 2 Weeks | 4 Weeks |
| 1 | 0.7 | i.a.[a] | |
| 2 | 0.1 | 0.2 | 0.2 |
| 3 | 0.2 | i.a. | |
| 4 | i.a. | | |
| 5 | 1 | —[b] | — |
| 6 | i.a. | | |

TABLE II-continued

| Compound No. | $LC_{50}$ (ppm) at Indicated Time | | |
|---|---|---|---|
| | 0 | 2 Weeks | 4 Weeks |
| 7 | 0.2 | — | — |
| 9 | i.a. | | |
| 10 | 0.2 | — | — |
| 12 | 1.5 | — | — |
| 13 | 3.6 | — | — |
| 14 | 0.1 | — | — |
| 16 | 0.7 | 1.5 | — |
| 17 | 0.6 | 1.0 | — |
| 18 | 0.6 | 1.0 | — |
| 19 | 0.2 | 0.6 | — |
| 22 | 0.5 | i.a. | |
| 23 | 0.5 | 1.2 | |
| 24 | 0.5 | 0.5 | 1.0 |
| 26 | i.a. | | |
| 27 | 1.0 | — | — |
| 28 | 0.5 | — | — |
| 29 | 1.0 | — | — |
| 30 | 0.5 | i.a. | |
| 31 | i.a. | | |
| 33 | — | | |
| 34 | i.a. | | |
| 35 | i.a. | | |
| 36 | i.a. | | |
| 37 | i.a. | 38 | i.a. |
| 39 | i.a. | | |
| 40 | 1.1 | 0.8 | 0.8 |
| 41 | <1.1 | i.a. | — |
| 43 | — | — | i.a. |
| 44 | — | — | 1.3 |
| 46 | i.a. | | |

[a]i.a. = inactive.
[b]— = no data.

Black Cutworm Tests

In these tests, two soil mixtures containing the test compound in concentrations of 20 and 2 parts per million by weight, respectively, were prepared by the procedures described above for the rootworm tests. Two series of tests were conducted, one for each dosage of the test compound. In each series of tests, a 60-gram sample of the treated soil was placed in each of two 4-ounce wide-mouthed jars. In each jar, a small amount of an insect bean diet was placed in a cavity in the surface of the soil, and was covered with the soil. Five holes, approximately 15 millimeters deep, were made in the soil and a single second instar black cutworm larva [*Agrotis ipsilon* (Hufnagel)] was placed into each hole and then covered with the soil. The jars were held at about 80° F. for 48 hours, at which time the results were observed and recorded as the percent mortality. Two replicates were conducted. The results are set out in Table III.

TABLE III

| Compound No. | Percent Mortality at Indicated Dosage (ppm) | |
|---|---|---|
| | 20 | 2 |
| 4 | 80 | 0 |
| 7 | 90 | 0 |
| 9 | 70 | 0 |
| 10 | 30 | 0 |

Systemic Activity Tests

Systemic activity of compounds of Formula I was determined as follows:

Mite Tests

The roots of pinto bean plants (*Phaseolus vulgaris*) in the primary leaf stage were placed in a flask containing water plus the test chemical. Various dosages of the test chemical were used, two replicates per dose. The stem of the plant was wrapped with non-absorbent cotton fitted snugly into the neck of the flask, to prevent possible fumigant action by the test chemical. Then the plant was infested with 50–100 adult female two-spotted spider mites, held for 48 hours at 85° F., and 50% relative humidity when mortality in the mites was determined visually. A series of different dosages of the test compound in the water were used, and the $LC_{50}$ dosage (the dosage in parts per million by weight of the test chemical in the water required to effect fifty percent kill of the mites) was determined. The results are set forth in Table IV.

TABLE IV

| Compound No. | $LC_{50}$ (ppm) |
|---|---|
| 2 | 1.1 |
| 3 | 0.5 |
| 5 | 0.3 |
| 6 | 2.3 |
| 11 | 0.5 |
| 12 | 19 |
| 15 | 5 |
| 16 | 1.4 |
| 17 | 1.4 |
| 19 | 0.7 |
| 20 | 0.4 |
| 22 | 1.1 |
| 24 | 1.1 |
| 25 | 0.9 |
| 27 | 1.1 |
| 29 | 1.9 |
| 31 | 8.4 |
| 45 | 0.5 |

Aphid Tests

Broad bean plants in the 6 to 8 leaf stage were removed from pots and their roots were washed free of soil. Each was placed in a flask containing 100 ml of a water solution of the test compound. The plant stems were wrapped with non-absorbent cotton which fit snugly into the neck of the flask to prevent possible fumigant action by the test compound. The flask was positioned under a wooden stage with the stem of the plant extending up through a slot in the stage. A 6"×6" square of paper was placed flat on the stage around the stem of the plant. A plastic ring 5 inches in diameter and 2 inches high, coated on the inside with petroleum jelly, was placed around the plant to prevent the aphids from escaping. 50 to 100 aphids were placed within each ring. Then the plant was held for 48 hours at 85° F., and 50% relative humidity when mortality in the mites was determined visually. A series of different dosages of the test compound in the water were used, and the $LC_{50}$ dosage (the dosage in parts per million by weight of the test chemical in the water required to effect fifty percent kill of the aphids) was determined. The results are set forth in Table V.

TABLE V

| Compound No. | $LC_{50}$ (ppm) |
|---|---|
| 2 | 3 |
| 3 | 2.1 |
| 11 | 43 |
| 12 | 21 |
| 14 | i.a.[a] |
| 15 | 14 |
| 19 | 7 |
| 20 | 8 |
| 35 | 14 |
| 40 | 43 |
| 45 | 2.6 |

[a] i.a. = inactive.

Corn Earworm Tests

The roots of broad bean plants (*Vicia faba*) in the 6–8 leaf stage were placed in a flask containing water plus the test chemical. Various dosages of the test chemical were used, with two replicates per dose. The stem of the plant was wrapped with non-absorbent cotton fitted snugly into the neck of the flask, to prevent possible fumigant action by the test chemical. Five third-instar *Heliothis zea* larvae were placed on each plant, which was then caged to prevent escape of the larvae. The plants were held in an insectary for 48 hours, then visually examined to determine the number of dead and moribund larvae. A series of different dosages of the test chemical in the water were used, and the $LC_{50}$ dosage (the dosage in parts per million by weight (ppm) of the test chemical in the water required to effect fifty percent kill of the larvae) was determined. The results are set forth in Table VI.

TABLE VI

| Compound No. | $LC_{50}$ (ppm) |
|---|---|
| 2 | 50 |
| 3 | 25 |
| 14 | i.a.[a] |
| 15 | i.a. |
| 19 | 22 |
| 20 | 28 |
| 22 | 13 |
| 25 | 20 |
| 27 | 25 |
| 43 | 16 |

[a] i.a. = inactive.

In another embodiment of the invention, compounds of formula I are useful protecting plants from the harmful effects of nematodes—that is, unsegmented roundworms of the class Nematoda, which customarily inhabit soil and feed upon the roots of plants growing therein.

The compound of formula I is effective when applied to the infested soil, and at least in part may act by entering the vascular system of the plant and poisoning nematodes that feed on the roots of the plant. Thus, an exemplary species of the componds of Formula I was found to be effective when applied to soil and plants were grown in the treated soil, and also to be (somewhat less) effective when applied to the foliage of plants grown in infested soil.

The invention accordingly provides a method for controlling soil-dwellng nematodes, and a method for protecting plants from attack by soil-dwelling nematodes, that comprises introducing into the soil surrounding the plants that is infested with nematodes and/or applying to the foliage of plants growing in infested soil a nematicidally effective dosage of a compound of Formula I.

Nematicide Tests

Compound 2, an exemplary individual species of the compounds of Formula I, was tested as a nematicide, as follows:

Soil Drench Test

Two or three plants of grain sorghum (*Sorghum bicolor*) 6-7 centimeters in height growing in 55 cubic centimeters of loam soil in 5 centimeter pots were used in each test. The soil in each pot was drenched with 2 milliliters of a solution/suspension of 10 parts per million of the test chemical in a solution of 5% acetone in water containing 0.05% Triton X-155, and allowed to equilibrate. 24 hours after treatment, the soil was inoculated with 2 milliliters of water containing approximately 500 stage 2 juvenile *Meloidogyne graminicola* nematodes. The treated pots were held in a glasshouse for two weeks, when the roots of the plants were washed clean and the effects of the nematodes were evaluated visually. The effectiveness of the test chemical was expressed in terms of an A B C system wherein A=0-20% infestation, B=21-50% infestation, C=51-100% infestation. A chemical achieving an A rating in the primary screen was retested at lower concentrations to obtain a dosage control curve. Two replicates were used at each concentration. The results were analyzed using RANDBLOCK, with a version of Abbott's correction factor to account for the level of knot formation in the untreated controls.

In the tests, Compound 2 was given an "A" rating and subsequently determined to have an $EC_{50}$ rating (concentration, ppm, in the test solution) of 0.33.

Foliar Spray (Systemic) Test

Pots containing *S. bicolor* plants described in the soil drench test protocol were used. A layer of non-absorbent cotton wool was placed in each pot to protect the soil and lower part of each plant from spray contamination, and the plants were sprayed with a standard solution/suspension of the test chemical, using an overhead track sprayer. The treated pots were left to dry for one hour, held in a glasshouse for 4 days, when they were inoculated with approximately 500 Stage 2 juvenile *M. graminicola* nematodes, then held for 2 weeks and the effect of the test compound was evaluated as described in the soil drench test protocol.

The $EC_{50}$ dosage for Compound 2 was found to be 2 kilograms per hectare.

I claim:

1. A compound of the formula

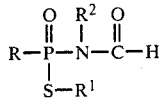

wherein R is alkyl or alkenyl of up to six carbon atoms, phenyl or benzyl, $R^1$ is straight-chain alkyl of three to five carbon atoms, branched-chain alkyl of three to six carbon atoms, phenyl or benzyl, and $R^2$ is hydrogen, alkyl, alkenyl or alkynyl of up to six carbon atoms, or alkyl of one to six carbon atoms substituted by phenyl; phenyl or phenyl substituted by one to three substituents selected from alkyl of one to six carbon atoms and halogen.

2. A method for killing insects and mites that comprises subjecting the insect to a lethal dosage of a compound of claim 1.

3. The compound of claim 1 wherein R is ethyl, $R^1$ is 1-methylpropyl and $R^2$ is methyl.

4. The compound of claim 1 wherein R is ethyl, $R^1$ is 1-propyl and $R^2$ is ethyl.

5. The compound of claim 1 wherein R is ethyl, $R^1$ is propyl and $R^2$ is methyl.

6. The compound of claim 1 wherein R is ethyl, $R^1$ is propyl and $R^2$ is 2-methylpropyl.

7. A method for protecting a plant from attack by insects and mites that comprises applying to the foliage of the plant an effective dosage of a compound of claim 1.

8. A method for protecting a plant from soil-dwelling insects and/or nematodes that comprises providing in the root zone of the plant an effective dosage of a compound of claim 1.

9. A method according to claim 8 wherein the compound of claim 1 is that wherein R is ethyl, $R^1$ is propyl or 1-methylpropyl and $R^2$ is methyl or ethyl.

10. An insecticidal and miticidal composition that comprises an effective dosage of a compound of claim 1 together with a carrier and/or a surface-active agent.

* * * * *